United States Patent
Hagen et al.

(10) Patent No.: US 8,362,282 B2
(45) Date of Patent: Jan. 29, 2013

(54) METHOD FOR STORING AND TRANSPORTING CYCLIC DIESTERS

(75) Inventors: Rainer Hagen, Berlin (DE); Udo Muhlbauer, Berlin (DE)

(73) Assignee: Uhde Inventa-Fischer GmbH (DE)

( * ) Notice: Subject to any disclaimer, the term of this patent is extended or adjusted under 35 U.S.C. 154(b) by 70 days.

(21) Appl. No.: 13/060,025

(22) PCT Filed: Aug. 12, 2009

(86) PCT No.: PCT/EP2009/005854
§ 371 (c)(1),
(2), (4) Date: May 13, 2011

(87) PCT Pub. No.: WO2010/020370
PCT Pub. Date: Feb. 25, 2010

(65) Prior Publication Data
US 2011/0288312 A1    Nov. 24, 2011

(30) Foreign Application Priority Data

Aug. 21, 2008 (EP) .................................. 08014855

(51) Int. Cl.
*C07D 319/00* (2006.01)

(52) U.S. Cl. ......................................................... 549/274
(58) Field of Classification Search ................... 549/274
See application file for complete search history.

(56) References Cited

U.S. PATENT DOCUMENTS

2008/0125599 A1 * 5/2008 De Vos ........................ 549/274

FOREIGN PATENT DOCUMENTS

| DE | 1 808 939 A1 | 6/1969 |
|----|---|---|
| DE | 101 00 752 A1 | 7/2002 |
| WO | WO-2008/065130 A1 | 6/2008 |
| WO | WO-2008/065132 A1 | 6/2008 |

OTHER PUBLICATIONS

"International Application No. PCT/EP2009/005854, International Preliminary Report on Patentability mailed Aug. 26, 2010", 5 pgs.
"International Application No. PCT/EP2009/005854, International Search Report and Written Opinion issued Dec. 22, 2009", 13 pgs.

* cited by examiner

*Primary Examiner* — Nizal Chandrakumar
(74) *Attorney, Agent, or Firm* — Schwegman Lundberg & Woessner, P.A.

(57) ABSTRACT

The present invention relates to a method for storing and/or transporting intramolecular cyclic esters (lactones), in particular lactide.

16 Claims, No Drawings

METHOD FOR STORING AND TRANSPORTING CYCLIC DIESTERS

PRIORITY CLAIM TO RELATED APPLICATIONS

This application is a national stage application under 35 U.S.C. §371 of PCT/EP2009/005854, filed Aug. 12, 2009, and published as WO 2010/020370 A1 on Feb. 25, 2010, which claims priority to European Application No. 08 014 855.4, filed Aug. 21, 2008, which applications and publication are incorporated herein by reference and made a part hereof in their entirety, and the benefit of priority of each of which is claimed herein.

The present invention relates to a method for storing and/or for transporting intramolecular cyclic esters (lactones), in particular lactide.

In the production of biodegradable polyesters, such as for example polylactides, the intermediate product dilactide is produced as standard. Dilactide can occur as L,L-dilactide, D,D-dilactide, meso-dilactide or as a mixture of two or three of the mentioned isomers. The properties of the polymers produced therefrom by ring-opening polymerisation depend greatly on the purity or the mixing ratio of the mentioned isomers. In order to be able to serve the market flexibly with PLA types of different properties and hence purposes of use, it is advantageous to store the isomers intermediately or to transport them between plants which are further removed from each other in molten form. However, it should be considered during storage that, in the case of standard storage, for example under a water- and oxygen-containing normal atmosphere, decomposition and ring-opening reactions of the dilactide can occur so that the dilactide is contaminated by the resulting decomposition products and is no longer suitable for the ring-opening polymerisation reaction for the production of the polylactide because of the high purity standards which must be maintained.

It is known from the literature that the storage of dilactide in molten state is of no use (NL 2000454), whilst, for other materials, such as e.g. epsilon-caprolactam, this form of storage is described as preferable (DE 101 00 752).

It is hence the object of the present invention to indicate a method for storing and transporting molten cyclic diesters, in particular dilactide, in which decomposition reactions are avoided for the most part.

This object is achieved with respect to the method for storing and/or transporting a cyclic diester by the features of patent claim 1. The dependent claims thereby represent advantageous developments.

According to the invention, a method for storing and/or transporting a cyclic diester of the general formula I is provided,

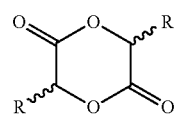

(I)

R being selected from hydrogen or linear or branched aliphatic radicals with 1 to 6 carbon atoms, in which the diester of the general formula I is transferred, after production, into a storage vessel, rendered inert, without interruption and directly in the liquid aggregate state and is stored in the storage vessel and/or transported at least at times at 40 to 150° C. The storage and/or the transport is thereby effected at a pressure of 0.1 bar to 10 bar, the water content of the diester which is used being max. 100 ppm, relative to the weight.

Surprisingly, it could be observed that, according to the method according to the invention, also a longer storage or transport time of several weeks is possible, the original properties of the dilactide which is used being able to be maintained essentially with respect to the acid content (carboxyl end group concentration) or the diastereomeric purity. According to the invention, dilactide is hence stored or transported in the liquid aggregate state and in closed containers.

The liquid phase is generally also termed "melt". In the method according to the invention, it can also be interspersed with solid particles, such as for example crystalline diester of formula I. Furthermore, solid particles, such as for instance crystalline diester of formula I, can be present for example as sediment. In the case of the method according to the invention, the predominant part of the diester of formula I to be stored or to be transported is preferably maintained in the liquid phase. For particular preference, 90% by weight, very particularly preferred over 99% by weight and in particular the entire diester of formula I is maintained in the liquid phase. If freezing of the melt in the container is allowed partially or completely, what matters is that this takes place without the admission of $O_2$ and $H_2O$, i.e. in particular with exclusion of ambient air. This applies also for the remelting of the frozen container content. If these conditions are maintained, decomposition can be avoided.

In order to keep the product in the liquid phase, a temperature is generally applied which corresponds to the melting point or is above the melting point. According to the invention, the storage temperature, according to the material used, is thereby between 40° C. to 150° C., preferred temperature ranges being between 40° C. to 130° C. Pure L-dilactide or the enantiomer thereof D-dilactide has a melting point of 98° C. The melting points of mixtures of the three mentioned enantiomers can be between 40° C. and 125° C. Consequently, it is particularly preferred if the storage or the transport of the diester, which can be dilactide for particular preference, according to the melting point of the pure substance used or the mixture used comprising different enantiomers or diastereomeric dilactides, is 20° C. above the melting point of the respective material or material mixture used.

The time duration for the storage and the transport, in the method according to the invention, is generally a few hours up to several weeks. It can possibly also be shorter or longer. The time duration is in particular at least three days, particularly preferred at least five days and very particularly preferred at least seven days.

It is particularly advantageous with the method that no change of the aggregate state of the diester used is effected so that the diester can be removed directly from the production process in liquid form and supplied to the storage vessel. It is particularly advantageous hereby that crystallisation of the product in supply pipes or lines of the process apparatus is completely prevented. Preferably, the diester is removed directly from the production process at a temperature of 90° C. to 160° C. in liquid aggregate state and transferred into the storage vessel.

The diester of formula I used in the method according to the invention in general has a preferred material purity of above 98% by weight, further preferred of above 99% by weight and particularly preferred of above 99.5% by weight. The proportion which makes up 100% by weight involves for example impurities, as are produced for example in the production of the product or for example by decomposition, ring-opening, oligomerisation or polymerisation of the diester. A measure of the purity of the diester of formula I can likewise be indicated by the carboxyl end group concentration. For the acid end group concentration in the diester of formula I which is used there are thereby responsible in particular, corresponding to the ester, alpha-hydroxycarboxylic acid of formula II

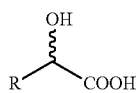
(II)

and/or corresponding oligomers of alpha-hydroxycarboxylic acid of formula III,

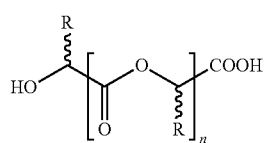
(III)

n=1 to 10 and R being defined respectively as above. The diester is thereby used preferably in a purity such that the carboxyl end group concentration of formula I is at most 20 mmol/kg, preferably at most 10 mmol/kg, particularly preferred at most 5 mmol/kg, in particular at most 2 mmol/kg.

In the case of the method according to the invention, it can be observed, according to the purity of the diester used, that the carboxyl end group concentration essentially remains constant, which can be equated with the fact that the diester of formula I, under the storage conditions according to the invention, is virtually not hydrolysed or oligo- or polymerised.

A further quality criterion of the diester used, with which excellent results are produced during storage, is the water content. This must, relative to the diester used, be below 100 ppm (as weight proportions), preferably below 50 ppm, in particular at most 20 ppm.

The storage vessel thereby preferably has an inert gas atmosphere, the inert gas requiring to be understood such that it cannot undergo a chemical reaction with the diester used. In general, inert gases generally known to the person skilled in the art can be used for this purpose, such as for example nitrogen and/or argon. Preferably, the gases thereby used are essentially free of oxygen and water, therefore have merely a negligibly low oxygen partial pressure or water content.

The storage pressure according to the invention is between 0.1 and 10 bar, pressures between ambient pressure and moderate excess pressure, for instance 1 bar to 5 bar, being preferred.

As preferred diester of the above formula I, in particular dilactide is used, it being irrelevant according to the invention whether here the D-, L- or the meso form of the lactide is used. The method can likewise be applied also to any mixtures of the above-mentioned different enantiomeric or diastereomeric lactides. In particular the method according to the invention is suitable for structure-stable storage of pure mesodilactide or mixtures of different lactide forms with a high meso content, i.e. for example a meso-lactide content of more than 60% by mol.

For the storage and transport, generally tightly sealable containers are used. Their size is generally irrelevant for the method according to the invention. Generally, containers in the $dm^3$ and $m^3$ range are used. The geometric form of the containers is also generally irrelevant for the method according to the invention. In order to minimise heat losses, containers should have a low ratio of surface to volume. Preferred examples are: (i) essentially spherical containers (e.g. so-called spherical tanks) and (ii) essentially cylindrical containers (e.g. bottles, barrels, so-called cylindrical tanks or tankers).

The wall of the container must be chemically inert relative to the ester of formula I and impermeable relative to gases and vapours, in particular oxygen and water vapour. Suitable materials are for example steel, stainless steel, aluminium or internally varnished metal barrels. In the case of internal varnishing or coating, care must be taken that these do not swell or become dissolved with the cyclic diester. It is likewise important that oxygen and water are neither adsorbed nor absorbed. Suitable coating materials are e.g. PTFE or PFA.

In the method according to the invention, the diester of formula I is preferably stored and transported in a heat-insulated container. There should thereby be understood containers which have a heat-insulating layer on the outside. As suitable heat-insulating layer there should be mentioned for example intermediate layers comprising a vacuum, comprising a not particularly heat-conductive gas or solid insulating materials, such as for example foamed polystyrene (e.g. Styropor®), glass- or mineral wool or a combination of these layers.

During the storage and transport of the diester of formula I in a heat-insulated container, the diester of formula I can be (i) located directly without further containers or (ii) packed in further containers. As suitable examples of (i) there may be mentioned heat-insulated tanks (e.g. spherical tanks, cylindrical tanks or tankers) or heat-insulated barrels. As suitable examples of (ii) there may be mentioned heat-insulated containers (e.g. ISO containers) which contain the diester of formula I in the form of further containers (e.g. barrels or bottles).

In the method according to the invention, the diester of formula I is stored and transported particularly preferably in a heat-insulated and heatable container. There should thereby be understood containers which contain heating in addition to the above-mentioned heat insulation. In the case of heat-insulated containers in which the diester of formula I is located (i) directly without further containers, the heating can be located for example in the form of heating elements directly in the diester of formula I to be stored or to be transported. Another possibility resides for example in the fact that the heating is located between the heat insulation and the internally situated container wall. There should be mentioned as examples for this purpose barrels or tanks provided with a heating jacket. In the case of heat-insulated containers in which the diester of formula I is located (ii) packed in further containers, the heating is normally found in the interior of these containers.

In a preferred embodiment of the method according to the invention, 220 litre barrels are stored or transported in a heatable ISO container.

The containers can be insulated and heatable, either by a double jacket or by an internally situated heating coil or both. Transport can be effected in tanker lorries by road or in tanker wagons by rail. The size and form of the containers is however not crucial.

Smaller unheated containers, e.g. 220 litre barrels, can be stored and transported in heatable containers or else transport and storage can be effected without heating, with the consequence that the contents freeze during longer transport and storage times. This is irrelevant for the quality of the product as long as the barrels remain tightly sealed. In order to make the contents usable again after storage and transport, the barrels can be put into a chamber heated with temperature-controlled warm air until complete melting of the contents. Care must thereby be taken that the contents of the barrels exceed the melting point by no more than 20° C. The product temperature at the heated wall should not be above 150° C.; any admission of air must be excluded also during the melting process.

In the case of short transport and storage times (<7 days) and large containers (from approx. 20 m³), permanent heating can be dispensed with.

Good insulation of the container suffices (dependent upon region and climate) to prevent freezing of the contents. Any parts of the contents which have possibly become solid are melted by pumping liquid around at the unloading station.

The method according to the invention for storing and transporting diester of formula I is particularly surprising since, according to general expert knowledge, a substantially greater reactivity would be anticipated precisely in the liquid and hence diffusion-mobile phase.

The method preferred according to the invention, in which the diester of formula I is maintained at the melting temperature of the diester of formula I or thereabove, is particularly surprising since, according to general expert knowledge, the reactivity generally rises with the temperature.

However what is crucial for the stability of the product is avoiding contact with water- and oxygen-containing media and not as low a storage and transport temperature as possible. This knowledge cannot be derived from general expert knowledge. It results herefrom that storage and transport should be effected in the liquid state since contact with water and oxygen can be minimised during this and during the preceding filling and subsequent emptying of the storage and transport containers.

The method according to the invention enables the storage and transport of diester of formula I, the method leading, even after a longer storage and transport time of several weeks, only to a small chemical change in the product.

The present invention is explained further with reference to the subsequent examples without restricting the invention to the subsequent parameters, in particular the specific ratios of the individual lactides relative to each other.

EXAMPLES

In a pilot plant, by rectification of crude lactide with a content of L-dilactide of 12.2% from the depolymerisation of a lactic acid prepolymer, two dilactide fractions (fraction A and B) were produced. Fraction A' was purified in a further rectification column. The purified product is diverted as side-flow (fraction C). The fractions were removed during a continuous operation of the rectification columns at a temperature of 145° C. (fraction A), 152° C. (fraction B) and 148° C. (fraction C) and were filled respectively into a 10 ml headspace flask which was dried in advance for 1 hour at 110° C. and subsequently rinsed for 20 minutes with argon. At the same time, respectively a sample was removed for analysis with respect to the carboxyl group concentration and meso-dilactide content.

Example 1

A flask filled with fraction B was sealed with a septum made of PTFE-coated butyl rubber and also the normal sealing discs and flange caps and placed for 24 h in a furnace preheated to 110° C. The COOH concentration before and after was respectively 2 mmol/kg. The meso-dilactide content was 4.1% before the test and 3.9% afterwards, the difference up to 100% being made up of L-dilactide.

Example 2

The procedure of example 1 was repeated but this time the flask was not sealed. After 24 hours in the furnace, the COOH concentration rose from 2 mol/kg to 69 mol/kg. The meso-dilactide content was 4.1% before and 3.5% afterwards.

Examples 1 and 2 show that quality losses during the liquid storage can be prevented only by excluding water and oxygen.

Example 3

The procedure of example 1 was repeated. This time a flask of fractions A, B and C respectively was placed for three days in a furnace heated to 110° C. The contents of the flasks were thereby liquid at all times. The carboxyl end group content was measured by means of titration and the meso-dilactide proportion by HPLC.

The results are shown in the following table:

| COOH | Before | After |
|---|---|---|
| Fraction A | 217 mmol/kg | 298 mmol/kg |
| Fraction B | 18 mmol/kg | 18 mmol/kg |
| Fraction C | 25 mmol/kg | 31 mmol/kg |
| Meso-dilactide content | Before | After * |
| Fraction A | 78.5% | 75.9% |
| Fraction B | 5.9% | 4.9% |
| Fraction C | 95.2% | 94.1% |

* The difference up to 100% is of L-dilactide.

Example 4

The test of example 3 was repeated, the purity of fraction B and fraction C with respect to the carboxyl end groups being greater.

| COOH | Before | After |
|---|---|---|
| Fraction A | 197 mmol/kg | 278 mmol/kg |
| Fraction B | 2 mmol/kg | 2 mmol/kg |
| Fraction C | 1 mmol/kg | 1 mmol/kg |
| Meso-dilactide content | Before | After * |
| Fraction A | 68.7% | 64.5% |
| Fraction B | 4.1% | 4.1% |
| Fraction C | 92.0% | 92.1% |

* The difference up to 100% is of L-dilactide.

It can be seen in particular with high meso-dilactide- and COOH concentrations that meso-dilactide is split more easily than L,L-dilactide. Whilst the COOH concentration increases, the proportion of meso-dilactide is reduced. It is also seen that, with a high L,L-dilactide content, the dilactide is still stable even at a COOH concentration of 18 mmol/kg, whilst a meso-dilactide-rich fraction with 25 mmol/kg COOH is not (example 3). Example 4 shows that, at COOH concentrations below 2 mmol/kg, also meso-dilactide has the required stability.

What is claimed is:

1. A method for storing and/or transporting a cyclic diester of the general formula I

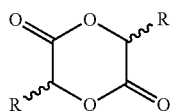

Formula I

R being selected from hydrogen or linear or branched aliphatic radicals with 1 to 6 carbon atoms, the method comprising:
transferring the diester of the general formula I, after production, into a storage vessel, rendered inert, without interruption and directly in the liquid aggregate state; and
storing the diester of the general formula I in the storage vessel and/or transporting the diester of the general formula I at least at times at 40 to 150° C., the storage and/or the transport being at a pressure of 0.1 bar to 10 bar and the water content of the diester which is used being max. 100 ppm, relative to the weight.

2. The method according to claim 1, wherein the storing comprises maintaining at least at times a storage temperature of 40° C. to 130° C.

3. The method according to claim 1, comprising removing the diester in the liquid aggregate state directly from the production process at a temperature of 90° C. to 160° C. and transferring the diester into the storage vessel.

4. The method according to claim 1, wherein the storage and/or the transport is effected at a pressure of 1 bar to 5 bar under inert gas.

5. The method according to claim 1, comprising rendering the storage vessel inert by purging with at least one gas which is essentially free of water and oxygen.

6. The method according to claim 1, wherein dilactide is used as diester of the general formula I.

7. The method according to claim 6, wherein the dilactide is produced by the following method steps:
a) polycondensing of lactic acid to form a prepolymer;
b) cyclicising depolymerisation; and
c) purifying of the dilactide.

8. The method according to claim 1, wherein the storing and/or transporting comprises storing and/or transporting L,L-dilactide, D,D-dilactide, meso-dilactide and/or mixtures thereof.

9. The method according to claim 1, wherein the carboxyl end group concentration of the diester of formula I which is used, resulting essentially from impurities due to alpha-hydroxycarboxylic acid, corresponding to the diester of formula I, of formula II

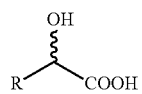

Formula II and/or from corresponding oligomers of the alpha-hydroxycarboxylic acid of formula III,

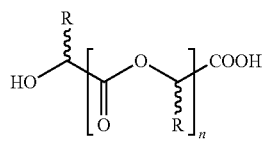

Formula III n=1 to 10 and R being defined respectively as above, is at most 20 mmol/kg.

10. The method according to claim 1, wherein the water content of the diester of formula I which is used, relative to the weight, is at most 50 ppm.

11. The method according to claim 2, wherein the storing comprises maintaining at least at times a storage temperature at most 20° C. above the melting point of the diester of formula I.

12. The method according to claim 5, comprising rendering the storage vessel inert by purging with at least one gas which is essentially free of water and oxygen, wherein the gas is chemically inert relative to the diester of the general formula I, and wherein the gas comprises at least one of nitrogen and/or argon.

13. The method according to claim 9, wherein the carboxyl end group concentration is at most 10 mmol/kg.

14. The method according to claim 13, wherein the carboxyl end group concentration is at most 5 mmol/kg.

15. The method according to claim 14, wherein the carboxyl end group concentration is at most 2 mmol/kg.

16. The method according to claim 10, wherein the water content of the diester of formula I which is used, relative to the weight, is at most 20 ppm.

* * * * *

UNITED STATES PATENT AND TRADEMARK OFFICE
CERTIFICATE OF CORRECTION

PATENT NO. : 8,362,282 B2
APPLICATION NO. : 13/060025
DATED : January 29, 2013
INVENTOR(S) : Hagen et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 152 days.

Signed and Sealed this
First Day of September, 2015

Michelle K. Lee
*Director of the United States Patent and Trademark Office*